United States Patent [19]

Perkins

[11] 4,313,799
[45] Feb. 2, 1982

[54] OXYGEN SENSOR AND METHOD FOR DETERMINING THE OXYGEN ACTIVITY IN MOLTEN GLASS

[75] Inventor: Richard A. Perkins, Newark, Ohio

[73] Assignee: Owens-Corning Fiberglas Corporation, Toledo, Ohio

[21] Appl. No.: 137,163

[22] Filed: Apr. 4, 1980

[51] Int. Cl.³ ............................................. G01N 27/58
[52] U.S. Cl. ................................. 204/1 T; 204/195 S
[58] Field of Search ............................ 204/1 S, 195 S

[56] References Cited

U.S. PATENT DOCUMENTS

| 3,216,911 | 11/1965 | Kronenberg | 204/1 S |
|---|---|---|---|
| 3,576,730 | 4/1971 | Spacil | 204/195 S |
| 3,578,578 | 5/1972 | von Krusenstierna | 204/1T |
| 3,784,459 | 1/1974 | Jackson | 204/195 S |
| 4,046,661 | 9/1977 | Stringer et al. | 204/195 S |
| 4,076,608 | 2/1978 | Fujishiro et al. | 204/195 S |
| 4,097,353 | 6/1978 | Kishida et al. | 204/195 S |
| 4,105,507 | 8/1978 | von Krusenstierna et al. | 204/1 T |
| 4,159,234 | 6/1979 | Eifler et al. | 204/195 S |
| 4,182,666 | 1/1980 | Dickinson et al. | 204/195 P |
| 4,208,265 | 6/1980 | Hori et al. | 204/195 S |

FOREIGN PATENT DOCUMENTS 1081545  8/1967  United Kingdom ............ 204/195 S

Primary Examiner—G. L. Kaplan
Attorney, Agent, or Firm—Ronald C. Hudgens; Patrick P. Pacella

[57] ABSTRACT

A method and apparatus for the measurement of oxygen activity in molten glass is disclosed. The apparatus or oxygen sensor is based upon an oxygen ion conducting solid electrolyte and solid electrodes. The sensor can be employed continuously during production in a glass melting furnace.

8 Claims, 9 Drawing Figures

OXYGEN SENSOR AND METHOD FOR DETERMINING THE OXYGEN ACTIVITY IN MOLTEN GLASS

TECHNICAL FIELD

This invention relates to an oxygen sensor and a method for determining the oxygen activity in molten glass.

BACKGROUND ART

Oxygen sensing devices for detecting oxygen concentration in a gas mixture are well known in the art. The oxygen sensor is constructed to generate an electrical signal responsive to the oxygen content of a gas. Stabilized zironium oxide has been employed as the main element of the oxygen sensor. This stabilized zironium oxide exhibits a conductivity by means of oxygen ions which transfer therethrough. As is well known, if some gas mixture whose partial oxygen pressure or absolute oxygen pressure must be measured is present on one side of an electrolyte and, simultaneously, a reference gas having a known partial oxygen pressure is present on the other side, a considerable voltage difference is generated by the driving force for movement of the oxygen ions between the gases through the electrolyte. The magnitude of the voltage difference is generally estimated by the Nernst equation:

$$E = (RT/4F)\ln(P_1 P_2)$$

where:
- R ... gas constant
- T ... absolute temperature
- F ... Faraday constant
- $P_1$ ... partial oxygen pressure of the reference gas
- $P_2$ ... partial oxygen pressure of the unkown gas Systems for determining the oxygen activity in molten metals, particularly in the production of steel, also are known in the art.

Gas probes are intended for long time usage. Most probes for molten metals, however, are intended for short term measurements, i.e., usually 30 to 60 seconds, as they cannot survive in the molten metal environment. In determining the oxygen activity of molten steel, for example, the probe is usually inserted just before pouring.

DISCLOSURE OF INVENTION

According to this invention, I have developed an oxygen sensor for the continuous monitoring of the oxygen activity in molten glass. My probe is an easy to use oxygen activity probe which can be inserted into the forehearth of a glass melting furnace in about 10 minutes. With platinum protection the probes of my invention have lasted for about a month.

In the production of textile glass fibers, the oxygen activity of the molten glass is believed to affect the glass and fiber properties. The yield strength of textile fibers is an important factor in the production of fiber in terms of fiber break rates and fiber quality. The yield strength appears to be dependent upon the oxygen activity of the glass. Thus, the production process and fiber quality might be better controlled and improved if the oxygen activity of the glass can be continuously monitored.

In electric wool furnaces the corrosion rate of the molybdenum electrodes appears to be dependent upon the oxygen activity of the glass. Likewise, spinner corrosion rates may be dependent upon the glass oxygen activity. Therefore, monitoring and controlling the oxygen activity of the glass may lead to improved electrode and spinner life.

Finally, the energy consumption and the production of glass fibers appears to be related to the ferrous iron content of the glass. This is related to the total iron content and the oxygen activity of the glass. Thus, monitoring of the oxygen activity of the glass during glass fiber production may have an impact upon the energy output.

BEST MODE FOR CARRYING OUT THE INVENTION

Figure 1:
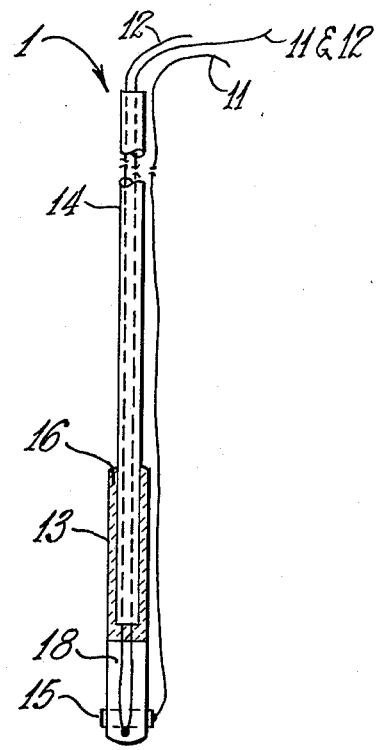
FIG. 1 shows an oxygen sensor of this invention which employs platinum gauze as the electrode on the molten glass side of the electrolyte.

FIG. 1 shows oxygen probe 1 with cell leads 11 and thermocouple leads 12 extending into a calcia-stabilized-zirconia (CSZ) cell 13 through alumina tube 14. A platinum gauge electrode 15 is placed on the glass contact side of CSZ cell 13. A Co/CoO mixture 18 was used as a reference in cell 13 and alumina cement 16 was used to seal cell 13.

Figure 2:
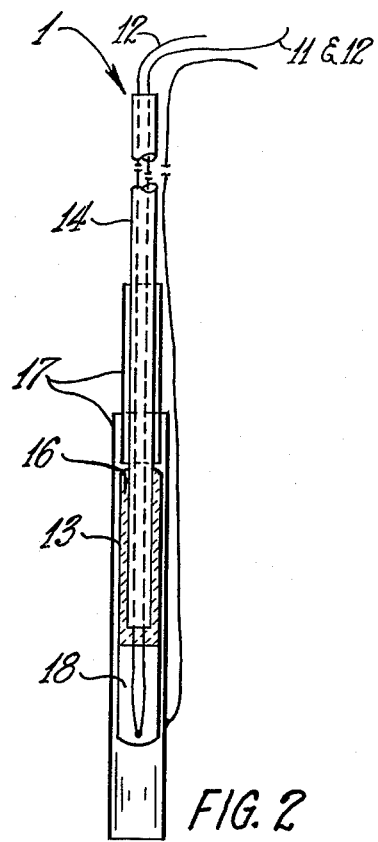
FIG. 2 illustrates the same oxygen sensor with the molten glass electrode being a platinum foil skirt.

FIG. 2 shows another embodiment of this invention where platinum electrode skirt 17 is used in place of electrode 15.

Figure 3:
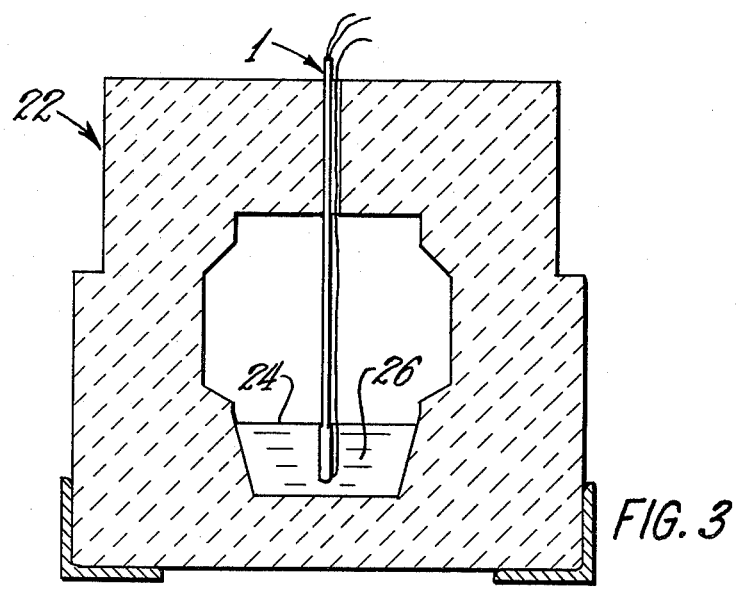
FIG. 3 shows the sensor of this invention in combination with the forehearth of a glass melting furnace.

FIG. 3 shows the probe of this invention inserted into forehearth 22 of a glass melting furnace (not shown) and extending below the surface 24 of molten glass 26. Generally, this invention is employed in a glass melting furnace from which molten glass issues.

My oxygen sensor has been developed to measure the oxygen activity in molten glass during production. This probe can be used to monitor production conditions and determine the effects of oxygen activity variations upon fiber production.

The CSZ is a ceramic solid electrolyte in which oxygen ions are the mobile species. An electrochemical cell can be established where the open circuit voltage across the cell is given by the Nernst equation previously mentioned where $P_2$ is the partial oxygen pressure of the molten glass. By establishing one side of the cell at a reference oxygen activity and measuring the open circuit voltage across the cell, the oxygen activity on the other side can be determined.

When a fired platinum paste electrode was first placed on the glass contact side of the CSZ cell, erratic results were obtained as the glass washed the platinum from the tube. A platinum gauze electrode was found to be suitable. The electronic conductivity of the CSZ at 1300° C. is low enough in the oxygen activity range of $10^{-16}$ to $10^{-4}$ atm to consider it as a totally ionic conductor. Outside of this range the electronic conductivity will allow oxygen to leak through the cell. When air or pure oxygen was used as a reference in the probe, the high electronic conductivity caused polarization of the probe as oxygen leaked through, and the results were unsatisfactory. When a $CO/CO_2$ gas mixture, a Co/CoO mixture or Ni/NiO mixture was used to establish the reference oxygen activity, the probe measured well. The low oxygen activity of these references ($10^{-7}$ to $10^{-12}$ atm) reduced the polarization problem. The CSZ material used has been partially stabilized with $3\frac{1}{2}$ wt CaO in the $ZrO_2$. Other solid electrolyte compositions have better ionic conductivity properties, but this composition has the best thermal shock resistance.

The CSZ tip was cemented to an alumina tube so that once the tip was hot the probe could be inserted more rapidly into the forehearth.

This probe design is very mobile, can be inserted into a forehearth fairly rapidly (about 10 min. from ambient temperature), has no electrode contact or gas flow problems, and yields valid readings quickly after insertion into the glass.

Another embodiment of the invention extends the life of the sensor. A $\frac{3}{8}"$ CSZ tip which has a wall thickness of 3/64" lasts about three weeks in an E glass textile forehearth at 1300° C. and about two weeks in a wool glass forehearth at 1100° C. The life of the probe can be appreciably extended by covering the underglass portion of the probe with Pt foil as shown in FIG. 2. Such coverings have extended the lifetime in wool glass forehearths to about one month. In this design the Pt foil is also used as the outside electrode. Thus, with Pt foil protection reasonable probe lifetimes have been attained.

Another embodiment of this invention prevents the diffusion of cobalt or nickel from the reference mixture through the zirconia. The diffusion occurs because of the high temperature in E glass forehearths (about 1300° C.). To minimize this effect, the metal/metal oxide powder has been sintered and wrapped in Pt gauze to reduce contact between the cobalt and zirconia.

EXAMPLE I

Laboratory measurements in sodium disilicate were made to determine if the probe could yield theoretical values as given by the Nernst equation. The oxygen activity of the melt was varied by passing $O_2$/Ar and $CO/CO_2$ gas mixtures over the melt in an airtight chamber. One probe measured the oxygen activity of the cover gas while the other measured the oxgyen activity of the glass melt.

Figure 4:
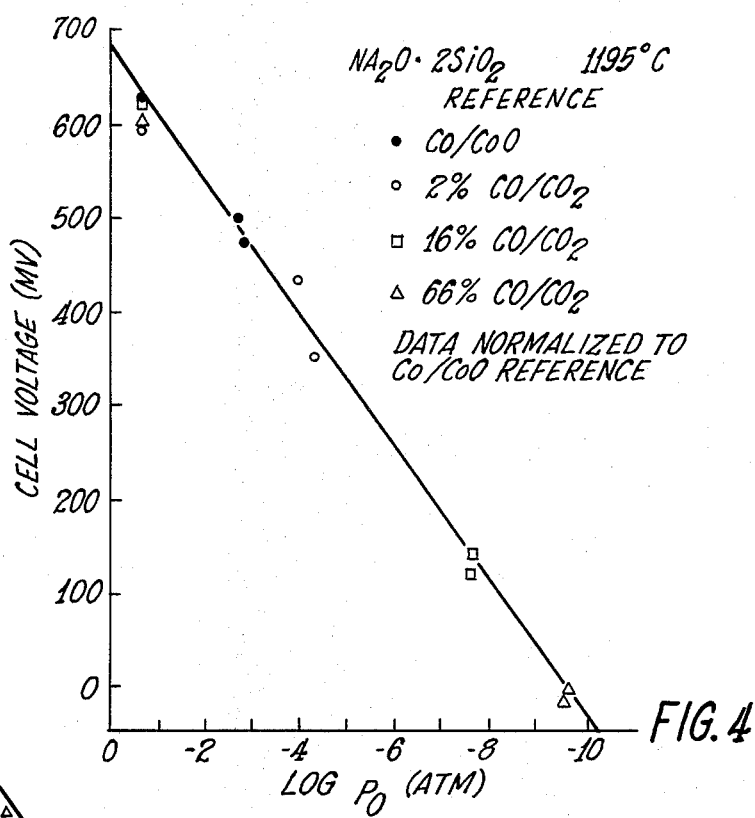
FIGS. 4 through 9 show data for the examples of this invention.

The oxygen activity of the gas and the glass were monitored with time as the composition of the cover gas was varied. The melt was always equilibrated with air before a change was made. When the oxygen activity of the glass showed no significant decrease over a four hour period, the oxygen activity of the melt was assumed to be in equilibrium with the cover gas. If the melt equilibrated with the gas and the probe response obeyed the Nernst equation, the probe output will be that calculated using the reference oxygen activity and the oxygen activity of the melt cover gas. FIG. 4 shows the probe output plotted versus the oxygen activity of the cover gas with the solid line indicating compliance to the Nernst equation. As can be seen, the results corresponded well to the Nernst relationship down to an oxygen activity of $1 \times 10^{-10}$ atm.

Figure 5:
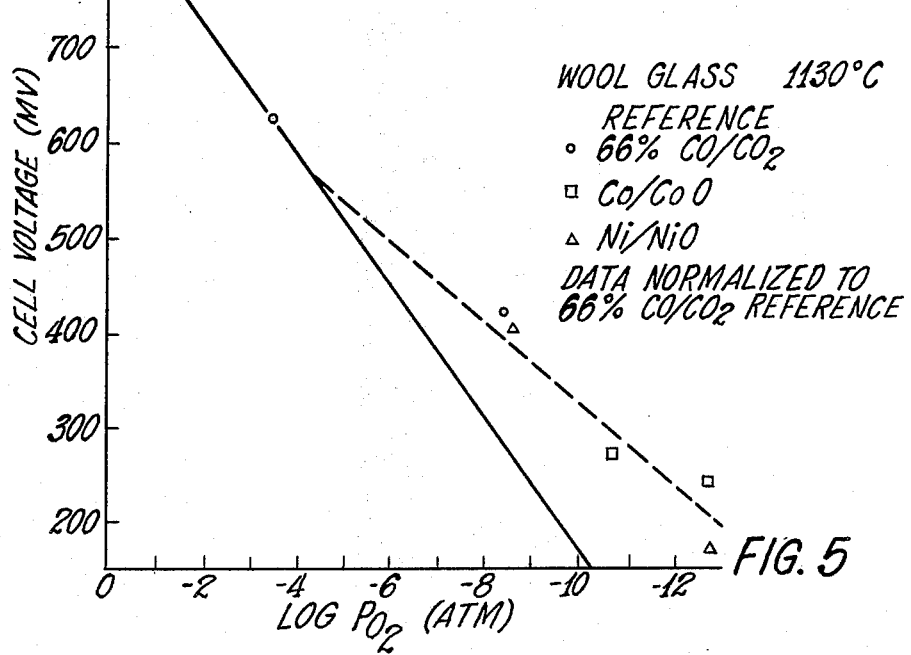
Figure 6:
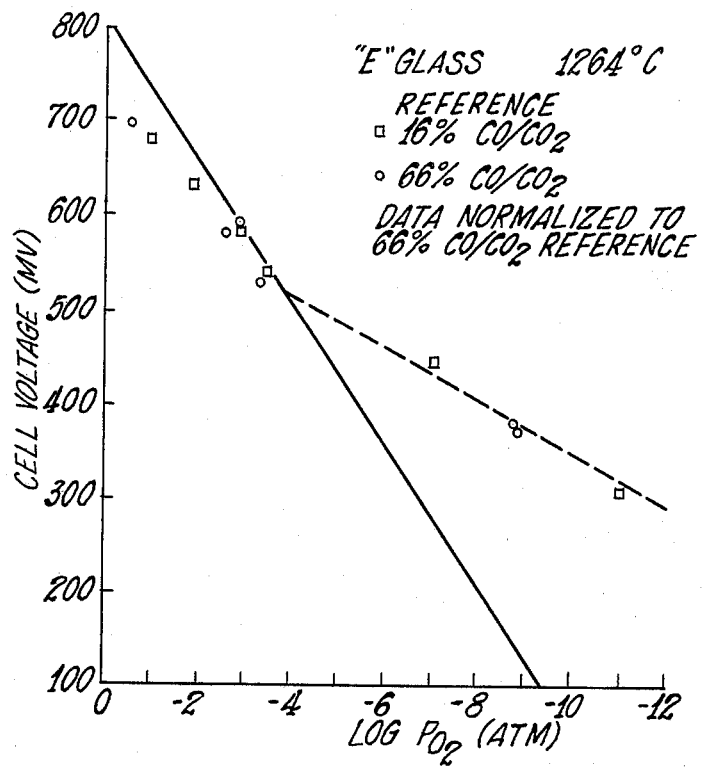

The results obtained for similar measurements in a wool glass and 200 E textile glass are shown in FIGS. 5 and 6, respectively. For both glasses a deviation from the Nernst relationship was observed as the oxygen activity of the cover gas decreased. The reason for this deviation was not known; however, the more complex chemistry of these glasses (compared to sodium disilicate) probably causes them to be somewhat buffered, and at long times the results would approach the Nernst relationship. These data were taken about eight hours after the cover gas was introduced into the furnace chamber. The similarity for the data in the two glasses and the reproducibility using differing reference oxygen activities indicate that these deviations are attributable to the glass and not an inaccuracy of the probe.

INDUSTRIAL APPLICABILITY

Field trials using the CSZ probe were carried out in a textile forehearth. The probes were inserted through the top of the forehearth down into the glass. The measurements were generally made at the end of the forehearth with the hole being between bushings. A 2% $CO/CO_2$ gas mixture was used as the reference gas for the probe. The oxygen activity of the glass was determined to be about $3 \times 10^{-4}$ to $7 \times 10^{-4}$ atm at about one inch below the glass level. Subsequent measurements yielded oxygen activities of $5 \times 10^{-4}$ and $4 \times 10^{-4}$ atm, respectively. When air or purified argon was used as a reference gas, the probe gave poor results. Thus, $CO/CO_2$ gas was used.

A set of measurements using the foil skirted sensor with the Co/CoO reference was made in several forehearths. The probe was inserted to the bottom of the forehearth and measurements were taken as the probe was moved up through the glass. The probe was allowed to equilibrate about an hour at each point of measurement.

Figure 7:
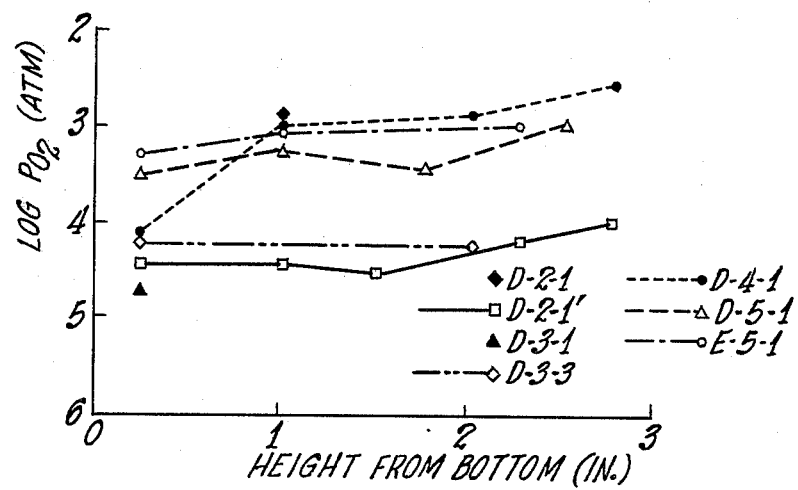

The results of the measurements are shown in FIG. 7. The results indicate that an oxygen activity gradient exists in the forehearth with the glass more oxidized toward the surface. Also, the glass is more oxidized toward the end of the forehearth.

Figure 8:
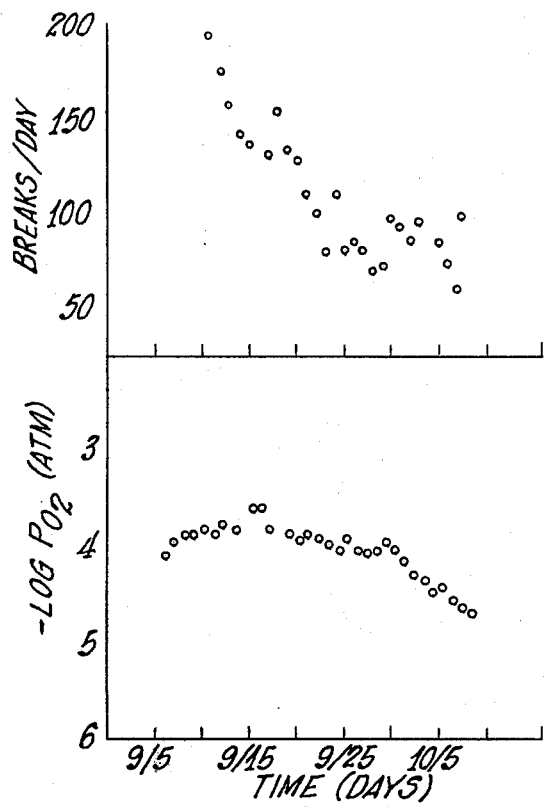
Figure 9:
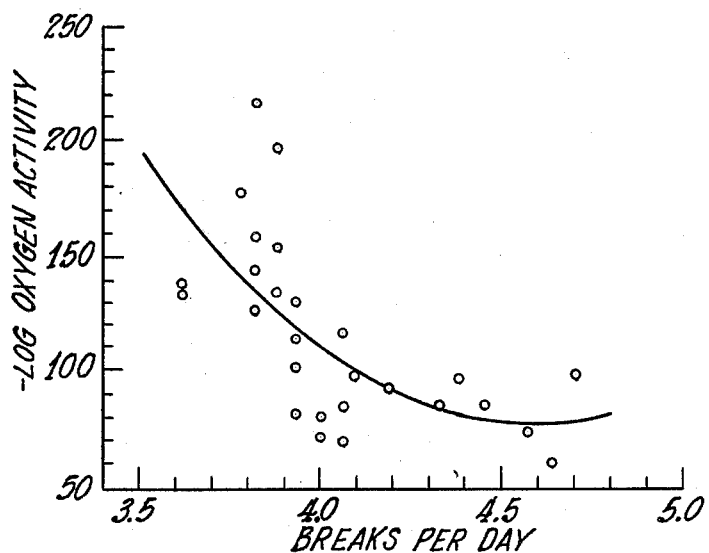

A probe for continuous monitoring was placed in a forehearth. Plots of the glass oxygen activity and bushing breaks per day are shown in FIG. 8. From the time of starting both the break rate and the oxygen activity have decreased. In FIG. 9 the break rate is plotted versus the oxgyen activity, and some correlation between the two can be seen.

A series of three measurements were made in an electric wool furnace. The probe was slowly entered through the batch cover, and the EMF was measured from the time the probe entered the glass until it failed due to destabilization of the CSZ as the calcia in the CSZ was dissolved by the molten glass. Destabilized zirconia is an electronic conductor and does not function as a oxygen partial pressure sensor. The probe lifetime was about 1 hour at 1400° C., which was the temperature of the glass at the locations at which the probes were placed in the tank. The results of the three measurements yielded an oxygen activity in the range of $10^{-5}$ to $10^{-4}$ atm with a value of about $4 \times 10^{-5}$ being preferred. In the last measurement, three different reference gases were used in the probe, and essentially equivalent values for the oxygen activity of the glass were obtained. This indicated that the probe was performing in a manner as predicted by the Nernst equation during these measurements. The good correspondence between the results of the three probes and the Nernst behavior exhibited by the third established a degree of confidence in the measurements.

The Pt foil skirted type probe was inserted into several wool glass forehearths. Because the first forehearth could not be easily accessed, the probe could be inserted only one to two inches below the surface of the glass.

The results of these measurements are listed in Table I.

TABLE 1

Oxygen Probe Measurements

| Probe | Temperature (°C.) | EMF (mv) | (molten) $P_2$ glass) (atm) | Time |
|---|---|---|---|---|
| 1 | 1137 | 0.54 | $8 \times 10^{-3}$ | ½ hour |
| 2 | 1140 | 0.54 to 0.45 | $8 \times 10^{-3}$ to $4 \times 10^{-4}$ | 7 days |
| 3 | 1139 | 0.46 | $6 \times 10^{-4}$ | ½ hour |

The output for the second probe was fairly steady; holding at about 0.54 v for a day, gradually decreasing to 0.45 v and staying there for about 3 days and then increasing back to 0.54 v.

A probe was then inserted into another forehearth from a better location so that the depth of the probe could be varied. When the probe was located about one inch below the glass surface, the oxygen activity was found to be about $3 \times 10^{-2}$ atm. When the probe depth was increased to about six inches, the EMF of the probe dropped sharply which indicated that the oxygen activity had decreased. The oxygen activity at about 4 inches down was about $5 \times 10^{-5}$ atm. These data indicate that a substantial oxygen activity gradient exists from top to bottom in the glass stream in the forehearth with the glass substantially more oxidized at the surface. The glass at the bottom of the forehearth has about the same oxygen activity as that measured back in the furnace.

Probes have been inserted into a wool furnace foreheath for long term oxygen activity measurements, and data have been collected over a period of three months. The first probe was not inserted very deeply into the glass. The first probe failed after 17 days in the glass at 1120° C.

The second probe was positioned at about 4 inches below the glass surface. This probe, which was protected with platinum foil, failed after 29 days of service.

The third probe was inserted at a depth of 4½ inches. The third probe failed after 35 days.

As a result, the sensor of this invention can be employed continuously during production in a glass melting furnace.

I claim:

1. An oxygen sensor for determining the oxygen in molten glass comprising:
   a solid electrolyte;
   a solid, first electrode on the inside of the electrolyte adapted to be exposed to a reference gas or solid;
   a solid, second electrode on the outside of the electrolyte adapted to be exposed to molten glass; and
   electrical conducting means connected to the electrodes for conducting an electrical signal generated by movement of oxygen ions through the solid electrolyte, wherein the second electrode is platinum foil in the form of a skirt.

2. A sensor according to claim 1, wherein the solid electrolyte is an elongated tubular electrolyte having an axial closed end and an axial open end.

3. A sensor according to claim 2, wherein the sensor is connected to an alumina tube extended thru the axial open end and wherein the axial open end is sealed with alumina cement.

4. A sensor according to claims 1 or 2, wherein the electrolyte is calcia stabilized zirconia.

5. A sensor according to claim 1, wherein the reference gas or solid is a $CO/CO_2$ gas mixture, or a Co/CoO or Ni/NiO powder mixture.

6. A sensor according to claim 1 wherein the reference solid is wrapped to reduce contact between the electrolyte and reference solid.

7. A method for determining the oxygen activity in molten glass comprising the steps of:
   (a) adapting an oxygen sensor to be exposed to molten glass;
   (b) inserting the oxgyen sensor in molten glass wherein the oxygen sensor comprises,
      a solid electrolyte,
      a solid, first electrode on the inside of the electrolyte adapted to be exposed to a reference gas or solid,
      a solid, second electrode of platinum foil on the outside of the electrolyte, and
      electrical conducting means connected to the electrodes for conducting an electrical signal generated by movement of oxygen ions through the solid electrolyte; and
   (c) monitoring the oxygen activity in the molten glass, wherein the adapting is done by the platinum foil being in the form of a skirt.

8. A method according to claim 7, wherein the monitoring is measured continuously.

* * * * *